July 11, 1961 M. HAUALAND Plant Pat. 2,073
COLUMNEA PLANT
Filed May 12, 1960
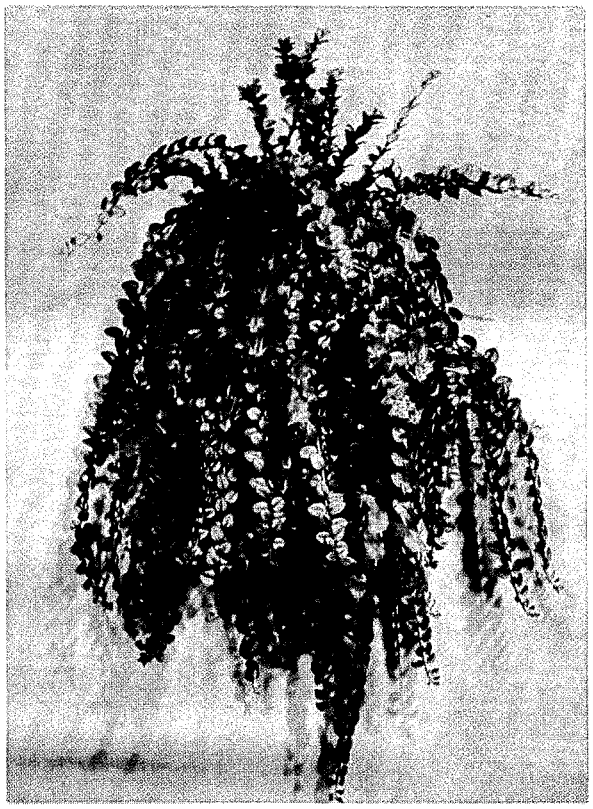
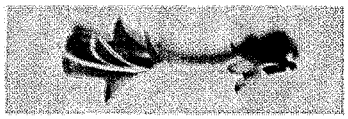
INVENTOR:
MAGNE HAUALAND
BY Howson & Howson
ATTYS.

United States Patent Office

Plant Pat. 2,073
Patented July 11, 1961

2,073
COLUMNEA PLANT

Magne Haualand, Hillevag, Stavanger, Norway, assignor to Robert Craig Company, Norwood, Pa., a corporation of Pennsylvania Filed May 12, 1960, Ser. No. 28,812
1 Claim. (Cl. 47—60)

The present invention relates to a new and distinct variety of plant of the genus Columnea.

This new and distinct variety of Columnea plant was originally produced by cross breeding. The seed parent of the plant of the present invention is the *Columnea microphylla* plant, also known as the *Columnea gloriosa diminutifolia* plant while the pollen parent is the *Columnea vedrariensis*. This new Columnea plant was originally produced by the applicant by cross breeding the above two plants and has been asexually reproduced many times by rooting cuttings in nurseries at Stavanger, Norway and at Norwood, Delaware County, Pennsylvania.

The seed parent, the *Columnea microphylla* plant, is not a vigorous plant and has very weak stems with small woolen-like dark green leaves covered with a considerable amount of fine hair. The flowers are attractive, having short stalks and are of a clear red color with a considerable amount of yellow in the throat. The growth of the stems of this plant is rapid, being approximately 40 to 80 centimeters a year.

As compared with the *Columnea microphylla* plant, the pollen parent, the *Columnea vedrariensis* plant, is a hardy plant with a strong stem having smooth, large, bright, light green leaves. The growth of the stems of this plant is relatively slow, being about 25 to 40 centimeters a year. The flowers of this plant are not attractive, having extremely long stalks causing the flowers to hang down instead of standing erect. Also the flowers do not have a clear, well-defined color but are a reddish color with varying size yellow veins.

In producing this new Columnea plant, the applicant has combined the rate of growth of the seed parent with the hardiness and strength of the stems of the pollen parent obtaining attractive flowers having short stalks, standing erect and being generally of a uniform scarlet color with a very small amount of yellow in the throat of the flower. The leaves of this new plant are relatively small, approaching the size and color of the seed parent, but have no readily discernable hairs and are smooth and shiny like those of the pollen parent.

The accompanying drawings illustrate a mature Columnea plant of the present invention and a single flower from the plant.

The following detailed description of the Columnea plant of the present invention refers to color plates of "A Dictionary of Color" by A. Maerz and M. Rea Paul, first edition, 1930.

The Columnea plant of the present invention is a small leafed vining plant with small generally ovate leaves having their greatest width at their base. The leaves are smooth and fairly shiny having no outstanding veins. To the naked eye the leaves appear smooth and shiny but upon close inspection some very fine hairs can be seen on the surface of the leaves. These hairs are not readily discernable and do not detract from the smooth and shiny appearance of the leaves. The color of the leaves varies with the strength of the light in which the plant is grown but generally is a uniform dark green and between a color equal to that of Plate 21–L–8 and a color equal to that of 23–J–10 with the underside of the leaves being of a color equal to that of Plate 21–L–7. The leaves grow outwardly from nodes on the stem with a pair of leaves extending outwardly in opposite directions from each node and adjacent pairs of leaves along the length of the stem being spaced 90° around the stem from the next adjacent pair of leaves. The leaves are relatively small with the full grown leaves varying between 15 to 20 millimeters long and between 12 to 15 millimeters wide.

A mature Columnea plant of the present invention has many stems starting at the root clump with no central main stem. The stems are generally straight and strong with a few of the stems having one or more branches. The stems are strong enough so that the newer, shorter stems of the Columnea plant will stand generally upright while the longer stems will trail downwardly. The stems, as set forth previously, will grow approximately 40 to 80 centimeters a year. The new stems are of a color approximately equal to that of Plate 21–K–5 while the old stems are of a color approximately equal to that of Plate 8–L–12.

There are many flowers on a mature, carefully grown Columnea plant of the present invention when it is in bloom with the flowers growing out of the leaf nodes and it is possible to have flowers growing out of a majority of the leaf nodes. The flowers are supported on the stems which may be approximately 1 to 1½ centimeters long and which maintain the flowers generally erect. Five sepals are positioned about the base of each flower with the sepals having a color approximately equal to that of Plate 17–L–5. The flower buds are of an extremely dark color when they are small and gradually get lighter and brighter as they approach maturity with the color of the buds varying from that of Plate 47–L–5 in the small buds to that of plate 5–L–6 in the more mature buds. The flowers possess bilateral symmetry and are shaped as illustrated in the attached drawings, being formed of a single petal which is generally trumpet shaped having a tubular base portion and terminating at the upper rear of the flower in three distinct scallops. A narrow spur projects outwardly from the petal at the throat of the flower. The flowers vary between 7 to 9 centimeters in length and are approximately 2 to 3 centimeters wide at their widest portion. The flowers are attractive and are of a bright scarlet color slightly darker at the base than at the top and at the top are of a color equal to that of Plate 1–L–12, and at their base are of a color approximately to that of Plate 2–L–12. At the throat of the flowers there is a small dot of yellow color approximately equal to that of Plate 1–L–6. The flower has a single central stamen which terminates at approximately the top of the flower and four long, slender pistils surrounding the stamen and terminating short of the end of the stamen. The stamen is of a color approximately equal to that of Plate 18–C–2 while the pistils are of a color approximately equal to that of Plate 18–K–1.

The new variety of Columnea plant of the present invention is distinguished primarily by its small, smooth leaves, its medium strong stems which provide the plant with a very attractive appearance and its abundance of scarlet flowers with each flower having only a small dot of yellow at its throat and by its rapid rate of growth.

I claim:

A new and distinct variety of Columnea plant substantially as shown and described, characterized particularly as to novelty by its small, smooth leaves and its abundance of scarlet flowers each having a small dot of yellow at its throat.

No reference cited.